(12) United States Patent
Tillotson et al.

(10) Patent No.: US 12,087,438 B2
(45) Date of Patent: Sep. 10, 2024

(54) LIQUID DISPENSING SYSTEM CREATING AND MAINTAINING A PERSONALIZED BUBBLE WITH A DEFINED RADIUS AND CONCENTRATION

(71) Applicant: SENSORY DESIGN & TECHNOLOGY LTD, Saffron Walden (GB)

(72) Inventors: Jennifer Ruth Tillotson, Cambridge (GB); Stephen Temple, Impington (GB)

(73) Assignee: SENSORY DESIGN & TECHNOLOGY LTD, Saffron Walden (GB)

( * ) Notice: Subject to any disclaimer, the term of this patent is extended or adjusted under 35 U.S.C. 154(b) by 1184 days.

(21) Appl. No.: 16/634,788

(22) PCT Filed: Jul. 26, 2018

(86) PCT No.: PCT/GB2018/052097
§ 371 (c)(1),
(2) Date: Jan. 28, 2020

(87) PCT Pub. No.: WO2019/025763
PCT Pub. Date: Feb. 7, 2019

(65) Prior Publication Data
US 2020/0211703 A1    Jul. 2, 2020

(30) Foreign Application Priority Data
Jul. 29, 2017 (GB) ..................... 1712210

(51) Int. Cl.
*G16H 40/67* (2018.01)
*A61B 5/00* (2006.01)
(Continued)

(52) U.S. Cl.
CPC ............ *G16H 40/67* (2018.01); *A61B 5/165* (2013.01); *A61B 5/4803* (2013.01);
(Continued)

(58) Field of Classification Search
CPC ........ G16H 40/67; G16H 20/70; G16H 50/20; G16H 20/10; G16H 20/90; G16H 40/63;
(Continued)

(56) References Cited

U.S. PATENT DOCUMENTS 3,917,396 A * 11/1975 Donohue ............... G05B 19/07
399/78
2007/0138326 A1* 6/2007 Hu ....................... A01M 1/2038
239/690

(Continued)

FOREIGN PATENT DOCUMENTS

EP    2707066 A1    3/2014
GB    2474424 A  *  4/2011    ............. A61L 2/232
(Continued)

OTHER PUBLICATIONS

European Patent Office, International Search Report, Application No. PCT/GB2018/052097, 2 Pages.

*Primary Examiner* — Bob Zadeh
(74) *Attorney, Agent, or Firm* — Ziegler IP Law Group, LLC.

(57) ABSTRACT

A method and device for creating and maintaining a personalised bubble of scent, the method including: providing a wearable device including a perfume reservoir, a perfume dispenser coupled to the perfume reservoir, and a controller to dispense a volume of perfume from the device at intervals; controlling said wearable device to dispense a pulse volume of scent from said perfume reservoir at a pulse interval; and determining said pulse volume and said pulse interval to maintain a mass per unit volume concentration of
(Continued)

said perfume above a threshold level within a defined radius from said wearable device.

26 Claims, 10 Drawing Sheets

(51) Int. Cl.
| | | |
|---|---|---|
| *A61B 5/16* | (2006.01) | |
| *A61M 21/02* | (2006.01) | |
| *B05B 12/00* | (2018.01) | |
| *G16H 20/70* | (2018.01) | |
| *G16H 50/20* | (2018.01) | |
| *A24F 47/00* | (2020.01) | |
| *A61M 21/00* | (2006.01) | |

(52) U.S. Cl.
CPC ............ *A61B 5/4839* (2013.01); *A61M 21/02* (2013.01); *B05B 12/00* (2013.01); *G16H 20/70* (2018.01); *G16H 50/20* (2018.01); *A24F 47/00* (2013.01); *A61M 2021/0016* (2013.01); *A61M 2209/088* (2013.01)

(58) Field of Classification Search
CPC ..... A61B 5/165; A61B 5/4803; A61B 5/4839; A61M 21/02; A61M 2021/0016; A61M 2209/088; B05B 12/00; A24F 47/00; G06F 3/167; G06N 3/08; G10L 15/22; G10L 25/63

See application file for complete search history.

(56) References Cited

U.S. PATENT DOCUMENTS

| | | | |
|---|---|---|---|
| 2008/0142624 A1* | 6/2008 | Ivri ................. | A45D 34/02 239/690 |
| 2013/0150658 A1* | 6/2013 | Miledi ............... | A61M 21/02 600/27 |
| 2014/0060452 A1 | 3/2014 | Linssen et al. | |
| 2015/0086951 A1* | 3/2015 | Bulut .................. | G09B 19/00 434/236 |
| 2016/0145845 A1* | 5/2016 | Seibt .................. | E03D 9/031 422/4 |
| 2020/0211703 A1* | 7/2020 | Tillotson ............ | G16H 20/10 |

FOREIGN PATENT DOCUMENTS

| | | | | |
|---|---|---|---|---|
| JP | 2003502114 | * | 1/2003 | |
| JP | 2007054445 | * | 3/2007 | |
| KR | 20150099430 | * | 8/2015 | |
| WO | 2012152321 A1 | | 11/2012 | |
| WO | WO-2012152319 A2 | * | 11/2012 | ............ A01K 15/02 |

* cited by examiner

LIQUID DISPENSING SYSTEM CREATING AND MAINTAINING A PERSONALIZED BUBBLE WITH A DEFINED RADIUS AND CONCENTRATION

FIELD

The aspects of the disclosed embodiments relate to methods, apparatus, and computer programme code for dispensing, for example scent, from a wearable device.

BACKGROUND

One of the inventors has previously described, in WO2006/059059, a system for dispensing scent in response to sound and the like. There is a considerable body of work on scent dispensing devices, but little on wearable devices or the practical implementation of electronic scent systems. To address this, the applicant has undertaken detailed research in relation to wearable scent i.e. perfume dispensing devices.

SUMMARY

According to the aspects of the disclosed embodiments there is therefore provided a method of creating, and preferably maintaining, a personalised bubble of scent (perfume), the method may comprise providing a wearable device comprising a perfume reservoir. A perfume dispenser may be coupled to the perfume reservoir. The wearable device may comprise a controller to dispense a volume of perfume from the device at intervals. The method may comprise controlling said wearable device to dispense pulses of perfume each with a controlled, pulse volume of perfume from said perfume reservoir, the pulses being dispensed at pulse intervals, for example every T seconds. The method may further comprise determining (and controlling) said pulse volume and said pulse interval to maintain a mass per unit volume concentration of said perfume above a threshold level within a defined radius from said wearable device.

Broadly speaking detailed research on diffusion of perfume from a wearable device has established that it is possible to create and maintain a region or "scent bubble" which is effectively personalised to a wearer of the wearable scent dispensing device. The threshold level may be an average human nasal detection threshold for a scent of the perfume.

This can be maintained by dispensing controlled volumes of perfume at controlled times/intervals to maintain the (mass per unit volume) perfume concentration above a threshold minimum, which may be evaluated at the bubble radius, and which varies over time. For example pulses of perfume may be dispensed every T seconds where T may be greater than 5, 10, 20 or 40 seconds.

The concentration has an oscillatory component with a larger variation with larger time intervals, and in embodiments the pulse volume and interval are chosen to maintain the scent concentration above a minimum concentration at the defined bubble radius. In embodiments the minimum concentration is the detection threshold of the human nose for the scent.

More particularly, in embodiments the controlling is arranged to control a minimum level over time, or an integral over time, of a concentration C(r,t) which varies with radius r from the variable device and with time t, where $$C(r, t) = f\left(M, \frac{r^2}{4Dt}\right)$$

where M is the mass of perfume (material) per pulse volume, D represents the diffusivity of the perfume, and f( ) a function representing diffusion of the perfume (material) in 3D space. In embodiments the perfume (material) may be substantially undiluted in the perfume reservoir.

Calculations have established that, surprisingly, when the radius is less than 100 cm the dispensed volume may be extremely small to maintain the scent (perfume) bubble, in embodiments less than one nanolitre. Thus, very surprisingly, a wearable device of the type described above may, with a modest scent reservoir of around 1 millilitre, potentially create and maintain a scent bubble for a period of a year or longer. The particular target radius may be determined dependent upon the location of the wearable device and may be smaller when the wearable is located on the head rather than on the chest or wrist.

As described further later, the method may include detecting one or more speech characteristics of the wearer and creating and maintaining the personalised bubble of scent in response.

The wearable device may have a plurality of perfume reservoirs.

A user interface may be provided to enable a user to control the scent. In response to user scent control data from the user interface the method may selecting one or more perfume reservoirs from the plurality of perfume reservoirs and/or controlling a pulse volume and/or pulse interval for the selected reservoir(s), in order to control a scent of the scent bubble dependent upon user control from the user interface.

Different perfume reservoirs may hold different perfume ingredients. Then different pulse volumes and/or pulse intervals may be used to control dispensing from the different perfume reservoirs in order to compensate for different respective dispersal rates of the perfume ingredients in the reservoirs.

Whether or not a scent bubble is created and maintained a method may include inputting context data relating to a use context or environment of the wearable device and providing the context data to a dispensing/scent control neural network. The dispensing/scent control neural network outputs dispensing/scent control data in response to the context (or environment) data. A liquid/scent dispensed by a wearable device is controlled dependent upon the dispensing/scent control data. The context (environment) data may comprise, for example: time data, day data, location data, activity data, voice data, music data e.g. music genre/sentiment data, scheduled or other contemporaneous event data; or other data. Thus the context (environment) data may comprise music data identifying and/or classifying music currently heard by a wearer of the wearable device. The music data may be provided by an associated device, for example a user-associated device (i.e. wearer-associated device) such as a mobile phone may provide data identifying and/or classifying a genre/sentiment of music currently being listened to by the wearer of the wearable device. Additionally or alternatively such a user-associated device, and/or the wearable device itself, may process, locally or remotely, sound heard by the wearer to similarly identify and/or classify the music. Although in some implementations context (environment) data is processed using a neural network or other machine learning technique, in other implementations the context (environment) data may be used to control a scent dispensed by a wearable device without employing a neural network. For example the scent control data may be determined by learned or predetermined e.g. downloaded and/or stored mapping data for mapping the context (environment) data to the scent control data.

The neural network may have previously been trained based on data collected from a user's operation of the device and/or data from multiple users may be pooled for training the neural network. The neural network may alternatively be provided pre-trained for use in a wearable device. Such a neural network may be a copy of a neural network that has been trained elsewhere.

In a related aspect the present disclosure provides a wearable device comprising: a liquid reservoir; a liquid dispenser coupled to the liquid reservoir; and a controller to dispense a volume of liquid from the device at intervals; wherein said controller is configured to control said wearable device to dispense a pulse volume of liquid from said liquid reservoir at a pulse interval.

In some implementations the pulse volume and the pulse interval are controlled to maintain a mass per unit volume concentration of said liquid above a threshold level within a defined radius from said wearable device.

The liquid may comprise perfume. Other liquids which may be dispensed include, but are not limited to: essential oils; decongestants; deodorant or antiperspirants (e.g. for hyperhidrosis); insect repellent; hormones; pharmaceuticals; human pheromones; CBD oil/cannabidiol; cognitive-enhancing drugs, nootropics and "micro-dosing" psychedelic medicines (e.g. LSD, psilocybin) for therapeutic applications; food or other flavour replicating liquids; personal care active ingredients; moisturising liquid; sun protection liquid; anti-cellulite liquid; vitamin-enhanced liquid; anti-tobacco liquid; anti-UV/anti-pollution liquid; and hydrating mist, e.g. water.

In some implementations the wearable device has an acoustic transducer—for example a microphone may be built into the device or the device may be wired or wirelessly coupled to another device with an acoustic transducer such as a mobile phone. The acoustic transducer may be coupled to a processor to process a speech signal of a wearer of the wearable device to detect one or more speech characteristics of the wearer. The signal processing may be local, for example performed in the wearable device or on an associated device such as the mobile phone, or remote, for example performed on a remote server.

A result of the processing, more particularly detection of the one or more speech characteristics may be that a signal is provided for the controller to dispense one or more pulses of liquid. The liquid may be a perfume as previously described or some other liquid. For example the system may be configured to detect stress in a voice; the system may then dispense stress-reducing perfume such as lavender.

In some implementations the one or more speech characteristics may comprise one or more speech characteristics of mania or depression. The processor may thus be configured to process the speech signal to classify the wearer as in a manic or depressive state. A result of the processing, more particularly detection of the mania or depression, may again be that a signal is provided for the controller to dispense one or more pulses of liquid. The liquid may be a stress-reducing perfume such as lavender, or in other implementations the liquid may comprise a drug for treatment of the mania and/or depression.

Thus in a related innovative aspect there is provided a method of calming a person. The method may comprise providing the person with a wearable device comprising a liquid reservoir, a liquid dispenser coupled to the liquid reservoir, and a controller to dispense a volume of liquid from the wearable device at intervals. The method may further comprise capturing speech data from the person as the person is speaking. The method may further comprise processing the captured speech data to detect one or more characteristics of the speech and, in response, to the detected characteristic. The method may further comprise controlling said wearable device to dispense a pulse volume of liquid from said liquid reservoir at pulse intervals. The method may further comprise controlling said pulse volume and said pulse interval to maintain a mass per unit volume concentration of said liquid above a threshold level within a defined radius from said wearable device.

Processing the captured speech data may comprise processing the speech data to detect a state of mania or depression in the person from a voice of the person, for example from a speed and/or one of speech of the person. The method may then further comprise creating and maintaining the personalised bubble of liquid in response to the detected state of mania or depression.

In a further aspect there is provided a wearable device comprising a plurality of perfume reservoirs each for a respective perfume or perfume ingredient; at least one dispenser coupled to the perfume reservoirs; and a controller to dispense perfume or a perfume ingredient from the wearable device at intervals. The controller may be configured to control the wearable device to dispense a pulse volume of the perfume or perfume ingredient from each perfume reservoir at a respective pulse interval.

In some implementations the device has a user interface to enable a user to control the scent. In response to user scent control data from the user interface the device may select one or more reservoirs from the plurality of reservoirs and/or control a pulse volume and/or pulse interval for the selected reservoir(s).

In some implementations, where the reservoirs are for perfume ingredients, the device is configured to use different pulse volumes and/or pulse intervals to control dispensing from the reservoirs in order to compensate for different respective dispersal rates of perfume ingredients in the reservoirs In some implementations the wearable device includes, or is coupled to, a dispensing/scent control neural network (or other machine learning system). The dispensing/scent control neural network (or other machine learning system) may be configured to receive context data relating to a use context of the wearable device, and in response to output dispensing/scent control data for controlling a liquid/scent dispensed by a wearable device.

A wearable device with multiple reservoirs as described above may be configured/controlled to create, and preferably maintain, a scent bubble as previously described.

Features of the previously described aspects and embodiments of the present disclosure may be combined with the above methods.

The aspects of the disclosed embodiments further provide processor control code to implement the above described methods, for example on a general purpose computing device, or on a mobile device, or on a digital signal processor (DSP). The code is provided on a non-transitory physical data carrier such as a disk, CD- or DVD-ROM, programmed memory such as non-volatile memory e.g. Flash, or read-only memory (Firmware). Code and/or data to implement embodiments of the present disclosure may comprise source, object or executable code in a conventional programming language (interpreted or compiled) such as C, or assembly code, or code for a hardware description language. As the skilled person will appreciate such code and/or data may be distributed between a plurality of coupled components in communication with one another.

BRIEF DESCRIPTION OF THE DRAWINGS

These and other aspects of the disclosed embodiments will now be further described, by way of example only, with reference to the accompanying figures in which.

DETAILED DESCRIPTION OF PREFERRED EMBODIMENTS

Figure 1A:
FIGS. 1a and 1b illustrate, respectively, a 40 cm 'bubble' radius dispenses scent from broach, pendant or collar/lapel, and a 15 cm 'bubble' radius dispensed scent from a left earring or spectacles which targets the nose for, localized delivery.

Scent dispensing systems are described which are considerably more economical than current alcohol-based perfume dispensers where on average one 0.2 ml 'spritz' of fragrance (of which 97% is ethanol) behind the ears is detectable to the human nose for several hours after application.

By calculating the average diffusion speed, density, and threshold of a perfume it is possible for embodiments of the described systems to sustain a 'scent bubble' at a fairly constant size. Using the described techniques a relationship can be calculated between regular pulses of perfume pre-set by the user and the length of time it takes to drain a reservoir i.e. the cartridge, in embodiments a consumable. Some assumptions about an example perfume are made. These are described in more detail later but include assumptions relating to:

formula; top, middle and base notes
composition
vapour density
fragrance ingredients
detection limits for the human nose.

As detailed below, the evolution of the detectable sphere (or 'scent bubble') of the perfume as it diffuses outwards is determined using diffusion calculations. The calculations are usable to determine the time required between perfume sprays that will establish and maintain a localised sphere of detectable levels of the given perfume.

Based on this spray interval, how long a perfume reservoir or cartridge of given size will last can also be determined: In the example below, a sphere or 'scent bubble' with a radius of 40 cm may be maintained by spraying one thousand 10 μm droplets every 45 seconds (the timing and the radius size—larger or smaller—can be adjusted depending on personal needs and design of the wearable technology).

For example, assuming 16 hours usage/day:
a perfume reservoir of 1 ml will last just under 1500 days (just over 4 years)
a perfume reservoir of 0.1 ml will last 150 days (approx. 5 months)
a perfume reservoir of 1 nl will last 1.5 days These long durations are facilitated because the system creates personalized local spheres which are held at just above the detection threshold, and because in implementations there is no need to use a solvent such as alcohol to dilute the perfume. In the above example each spray only uses 0.5236 nanolitres of perfume.

Figure 1B:
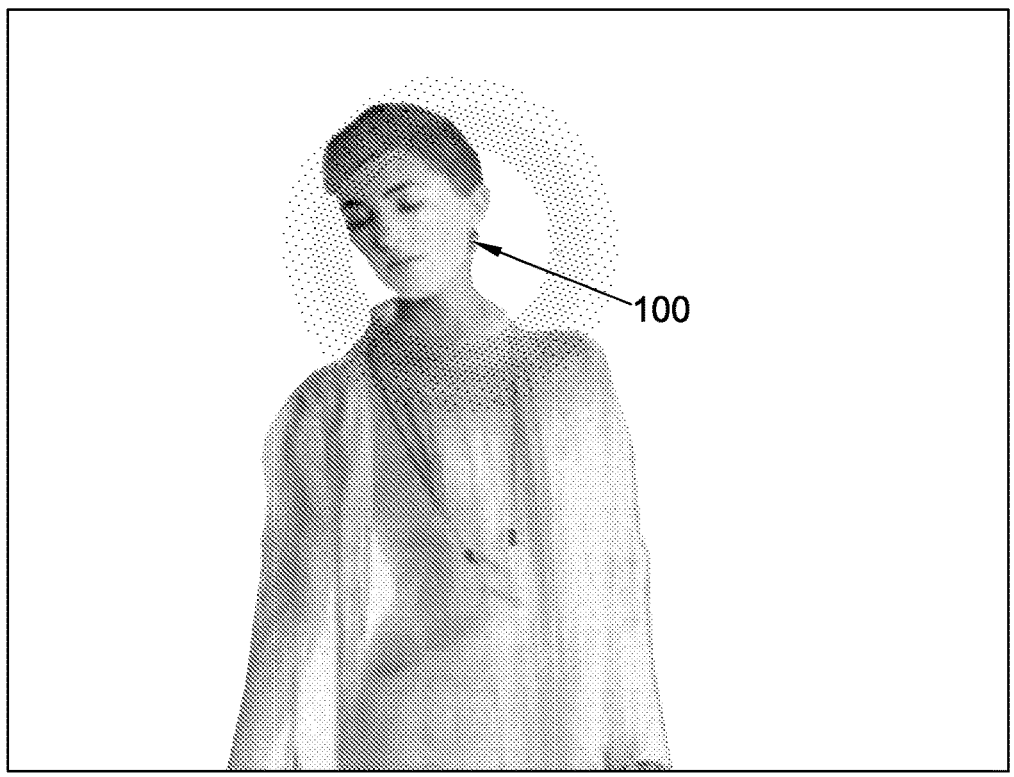

In embodiments of the system the radius and cartridge capacity may determine design parameters for the system. Referring to FIG. 1, there is a choice as to where the device 100 is placed on the body, in relation to the nose, and of the type of wearable, for example jewelry or clothing element (button, lapel, pocket), and so forth. Some options include:

an average bubble radius (40 cm)—is within arm's reach—ideal for a pendant or broach (FIG. 1a)
a bigger bubble radius (60 cm+)—is for a wrist watch/clothes to fragrance a larger area
a much smaller bubble radius (15 cm)—is for earrings, headphones, or spectacles (FIG. 1b)

In embodiments the perfume characteristics such as the diffusion coefficient, liquid density and the threshold concentration may be measured and/or calculated values.

Example Perfumes

A notional perfume formula for a first example perfume is as follows:

| | oil ratio | |
|---|---|---|
| Top Note ingredients | 40 | |
| d-Limonene | 8 | |
| Linalyl acetate | 6 | |
| Citral | 6 | |
| Hedione | 20 | methyl-dihydrojasminate |
| Middle Note ingredients | 30 | innocuous |
| Geraniol | 9 | |
| Benzyl acetate | 7 | |
| Phenylethyl alcohol | 7 | |
| Hexyl cinnamic aldehyde | 7 | |
| Base Note ingredients | 30 | |
| Vanillin | 7 | |
| Exaltolide | 8 | |
| Ambroxan | 10 | |
| Indole | 5 | 10% solution dissolved in dipropylene glycol |

The relevant threshold detection data are (in $mg/m^3$):

| | |
|---|---|
| d-Limonene = 1-Methyl-para-isopropenyl-1-cyclohexene | 2.02E+01 |
| Linalyl acetate = 3,7-Dimethyl-1,6-octadien-3-yl acetate | 6.65E−02 |
| Citral = 3,7-Dimethyl-2,6-octadienal | 1.73E−01 |
| Hedione = Methyl-(2-amyl-3-oxocyclopentyl)-acetate | |
| Geraniol = 2-trans-3,7-Dimethyl-2,6-octadien-8-ol | 3.00E−01 |
| Benzyl acetate = Benzyl acetate | 1.10E+02 |
| Phenylethyl alcohol = beta-Hydroxy ethyl benzene | 4.00E−02 |
| Hexyl cinnamic aldehyde = alpha-n-Hexyl cinnamal | 1.20E−01 |
| Vanillin = 3-Hydroxy-4-methoxy benzaldehyde | 9.09E−04 |
| Exaltolide = omega-Pentadecalactone | 1.80E−01 |
| Ambroxan = Dodecahydro-3a,6,6,9a-tetramethyl naphthofuran | |
| Indole = 2,3-Benzpyrrole | 3.85E−03 |

These data may be determined by routine experiment.

Another example perfume formula, a variant of the first perfume, was also considered. The composition and details of the components are given in the tables below:

| Ingredient | % | Chemical name | Formula |
|---|---|---|---|
| Top Notes | 40.0 | | |
| d-Limonene | 10.0 | 1-Methyl-para-isopropenyl-1-cyclohexene | C10H16 |
| Linalyl acetate | 5.0 | 3,7-Dimethyl-1,6-octadien-3-yl acetate | C12H20O2 |
| Citral | 5.0 | 3,7-Dimethyl-2,6-octadienal | C10H16O |
| Hedione | 20.0 | Methyl-(2-amyl-3-oxocyclopentyl)-acetate | C13H22O3 |
| Middle Notes | 30.0 | | |
| Geraniol | 10.0 | 2-trans-3,7-Dimethyl-2,6-octadien-8-ol | C10H18O |
| Benzyl acetate | 5.0 | Benzyl acetate | C9H10O2 |
| Phenylethyl alcohol | 10.0 | beta-Hydroxy ethyl benzene | C8H10O |
| Hexyl cinnamic aldehyde | 5.0 | alpha-n-Hexyl cinnamal | C15H20O |
| Base Notes | 15.5 | | |
| Vanillin | 5.0 | 3-Hydroxy-4-methoxy benzaldehyde | C8H8O3 |
| Exaltolide | 5.0 | omega-Pentadecalactone | C15H28O2 |
| Ambroxan | 5.0 | Dodecahydro-3a,6,6,9a-tetramethyl naphthofuran | C16H28O |
| Indole | 0.5 | 2,3-Benzpyrrole | C8H7N |
| Solvent | | | |
| Dipropylene glycol | 14.5 | | |
| | 100 | | |

| Ingredient | M.W. | MP/deg. C. | BP/deg. C. | Specific gravity (SG) | Vapour density vs air |
|---|---|---|---|---|---|
| Top Notes | | | | | |
| d-Limonene | 136.24 | | 177 | 0.84 | 4.7 |
| Linalyl acetate | 196.29 | | 220 | 0.91 | 6.8 |
| Citral | 152.24 | | 228 | 0.89 | 5 |
| Hedione | 226.32 | | 300+ | 1.00 | |
| Middle Notes | | | | | |
| Geraniol | 154.26 | | 230 | 0.89 | 5.31 |
| Benzyl acetate | 150.17 | | 215 | 1.06 | |
| Phenylethyl alcohol | 122.17 | | 220 | 1.03 | |
| Hexyl cinnamic aldehyde | 216.33 | | 305 | 0.95 | |
| Base Notes | | | | | |
| Vanillin | 152.15 | 83 | 285 ($CO_2$) | (liqu)1.06 | 5.3 |
| Exaltolide | 240.39 | 37 | 280 | | |
| Ambroxan | 236.40 | | | | |
| Indole | 117.15 | 52 | 254(decomp) | | |
| Solvent | | | | | |
| Dipropylene glycol | | | | | |

Device Parameters

A set of example device parameters, employed in the diffusion calculations later, is as follows:

As explained further later, these example parameters result in the example values for cartridge life and perfume vapour density below; the relevant equations are also given:

| | symbol | value | conventional units | SI value | SI units |
|---|---|---|---|---|---|
| Cartridge volume | V | 1 | ml | 0.000001 | m^3 |
| droplet diameter | D | 25 | microns | 0.000025 | m |
| number of droplets per dispense | N | 1.00E+03 | — | 1000 | — |
| delay time between dispenses | t_delay | 0.13 | minutes | 8 | sec |
| density of liquid perfume | rho_l | 1 | g/cm^3 | 1000 | kg/m^3 |
| density of air | rho_air | 1 | | | |
| density of vapour perfume/rho_air | alpha | 5 | — | | |

| Output | Symbol | Value | Units | Value | Units |
|---|---|---|---|---|---|
| droplet volume | V_d | 8.18 | picoliters | 8.18123E−15 | m^3 |
| volume per dispense | V_p | 8181.23 | picoliters | 8.18123E−12 | m^3 |
| avg rate of consumption | Q | 1022.65 | pL/sec | 1.02265E−12 | m^3/s |
| time to consume cartridge | t_c | 16.98 | 16 hour days | 977847.9704 | sec |
| density of vapour perfume | rho_v | 5.00E+06 | mg/m^3 | 5 | kg/m^3 |
| mass of material per dispense | | | | 8.18123E−09 | kg |

The following was also assumed (where 1 mm^3 is one microliter):

| Volume of initial vapour | V_i | 1.636246174 | mm^3 | 1.63625E−09 | m^3 |
|---|---|---|---|---|---|

Evaporation process efficiency e=1.
The relevant equations are:

| Output | | Equation |
|---|---|---|
| droplet volume | V_d | 4/3π(D/2)^3 |
| volume per dispense | V_p | V_d*N |
| avg rate of consumption | Q | Q/t_delay |
| time to consume cartridge | t_c | V/Q |
| density of vapour perfume | rho_v | |
| mass of material per dispense | | |

Perfume Diffusion

Background information on diffusivity and the diffusion coefficient can be found in Wilke, C. R. and C. Y. Lee, "Estimation of Diffusion Coefficients for Gases and Vapors", Ind. Eng. Chem., 47, 1253-1257 (1955). The gas diffusivity is available from the Wilke-Lee modification (1955) of the Hirschfelder-Bird-Spotz method (1949). This uses molecular weight, molar volume at the normal boiling point, normal boiling point, temperature, and pressure as input parameters. To determine how long it would take for the smell of perfume to travel across a room one can compare molecular diffusivity of gas to convective currents, to turbulent diffusion.

The steady state of diffusion for distance (radius) r is:

$$C = r\_o * C\_o / r$$

where C_o=initial concentration, and r_o is a constant length which may be chosen according to the units so that the equation is correct for the units used. However the time is long to reach steady state conditions and it appears that that this is not a good description. Instead we consider an unsteady state of diffusion dominated in 3D space, with central symmetry (no angular dependence).

Scent Bubble

Consider the detection threshold at a defined bubble radius and the spray interval to achieve this. In the following example the parameters used are: bubble radius=15 cm, detection threshold=0.2 mg/m^3 (0.0000002 kg/m^3), diffusivity 5.00E−04 m^2/sec, M=8.18123E−09 kg.

The characteristic length (solve dc/dt=0) is $r^2=4Dt$; this is when a concentration stops increasing in an unsteady problem, so this can be considered as a limit between steady and unsteady states. The characteristic time is $r^2/4D=11.25$ second. Then, from solving Fick's 2nd law in spherical coordinates, with constant Mass input:

$$C = M/(4(\pi Dt)^{3/2} * \exp(-r^2/4Dt))$$

which approximates a Gaussian with a time decaying amplitude at centre.

The distance where the detection threshold is reached is:

$$r = \mathrm{sqrt}(4Dt * \log(M/(4*C\_detection*(pi*D*t)^{3/2})))$$

Figure 2A:
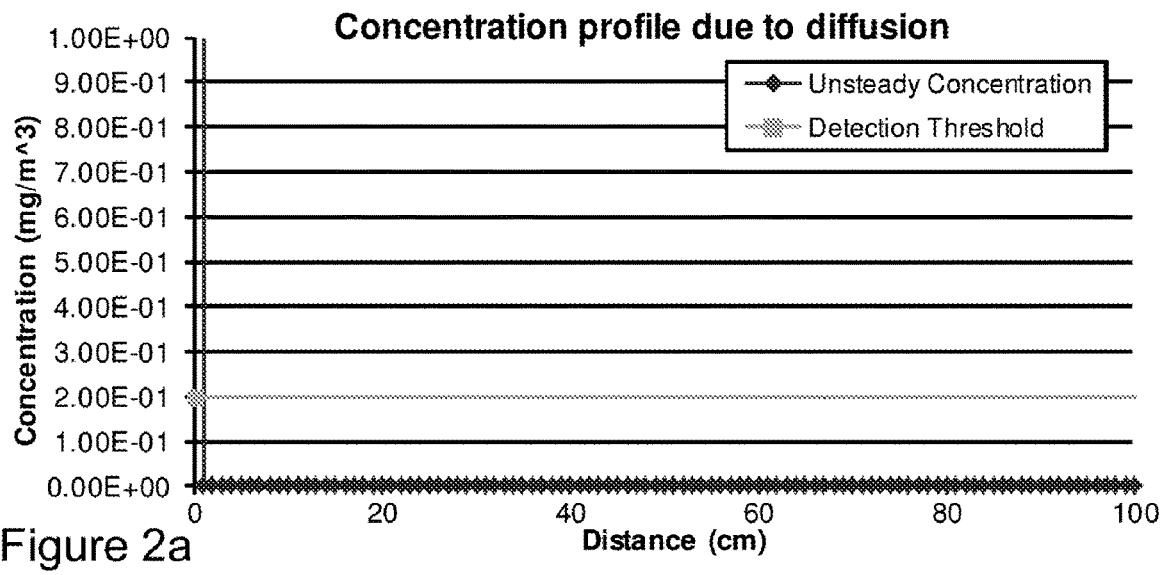
FIGS. 2a to 2l illustrate time evolution of a dispensed scent bubble.
Figure 2B:
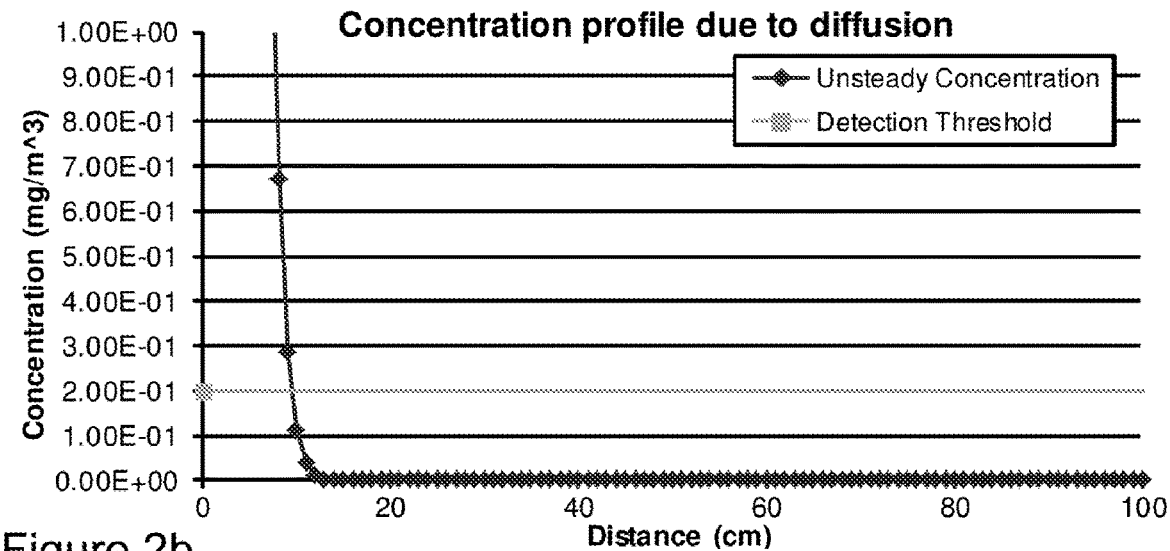
Figure 2C:
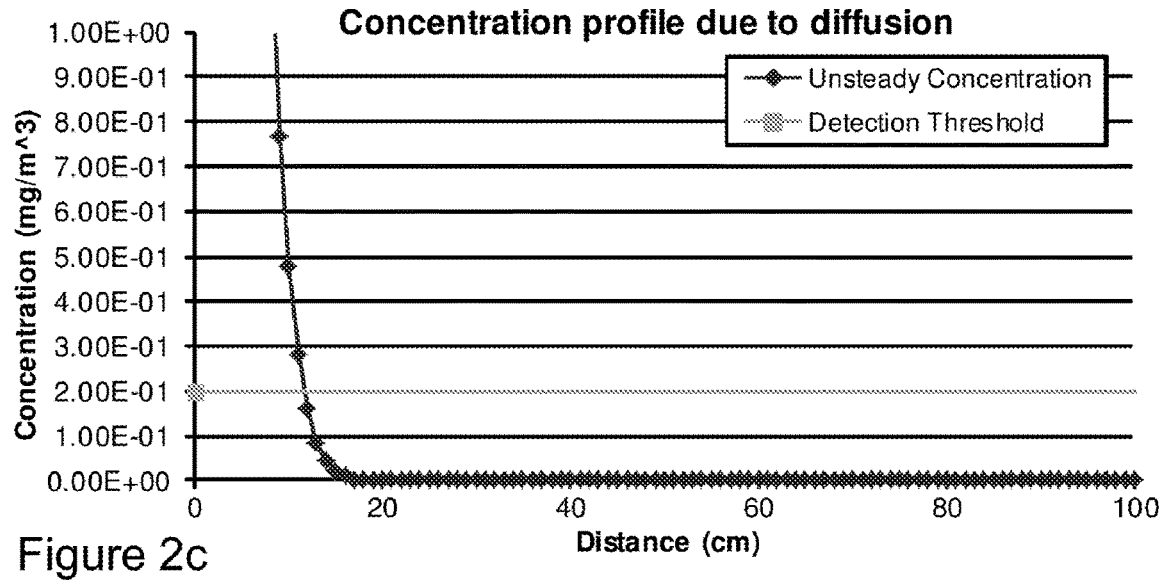
Figure 2D:
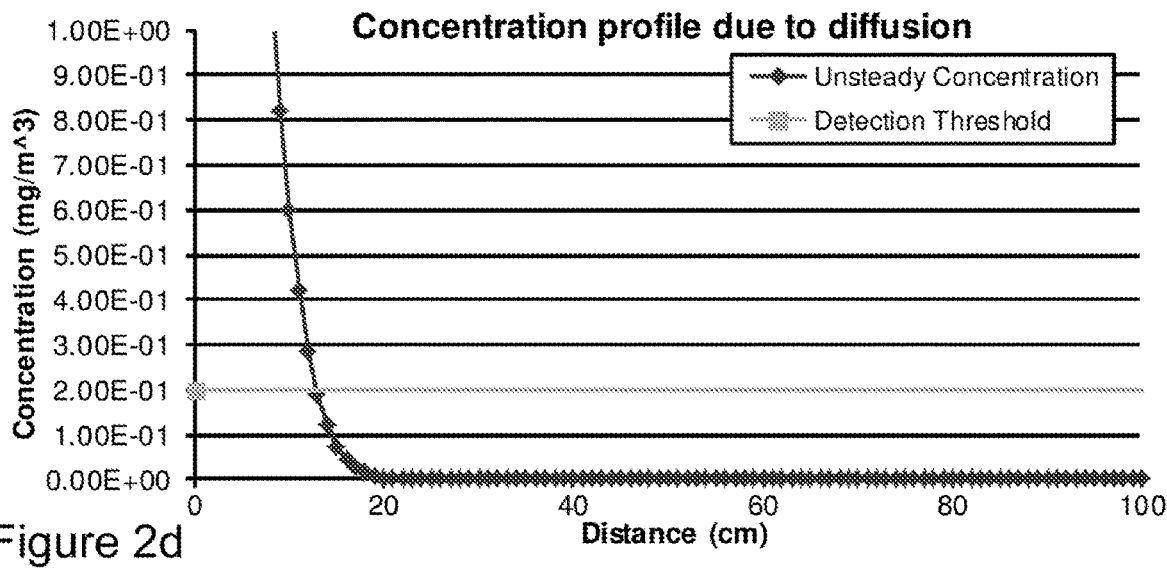
Figure 2E:
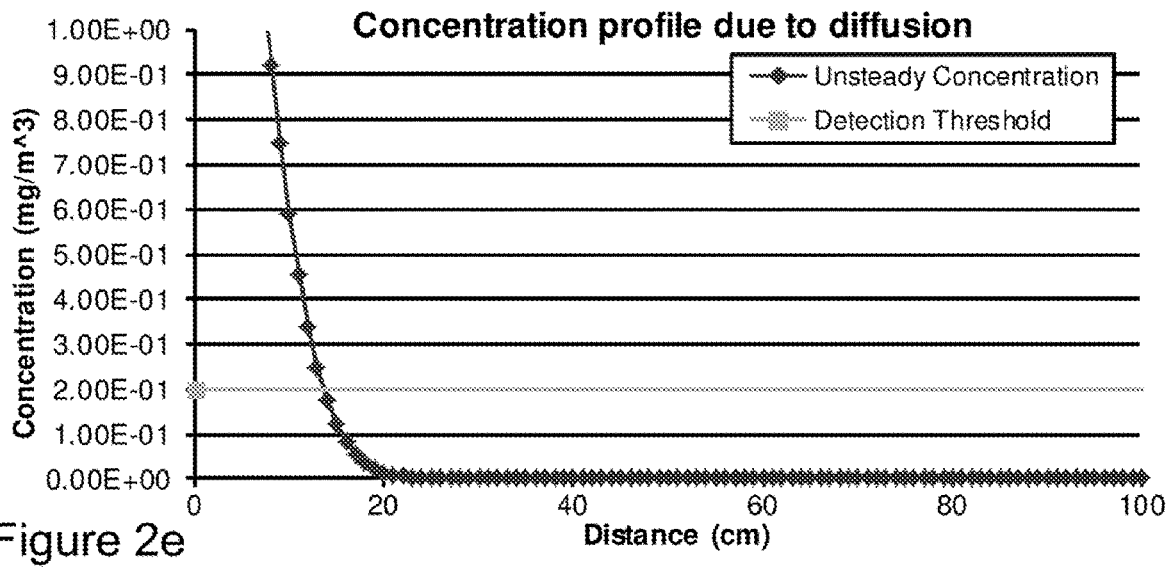
Figure 2F:
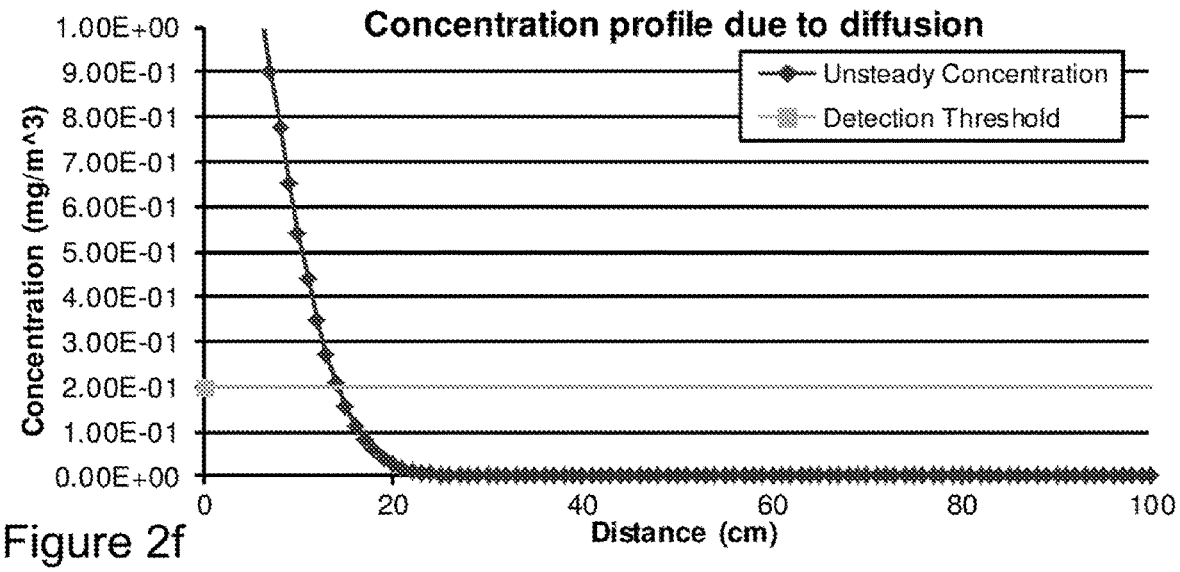
Figure 2G:
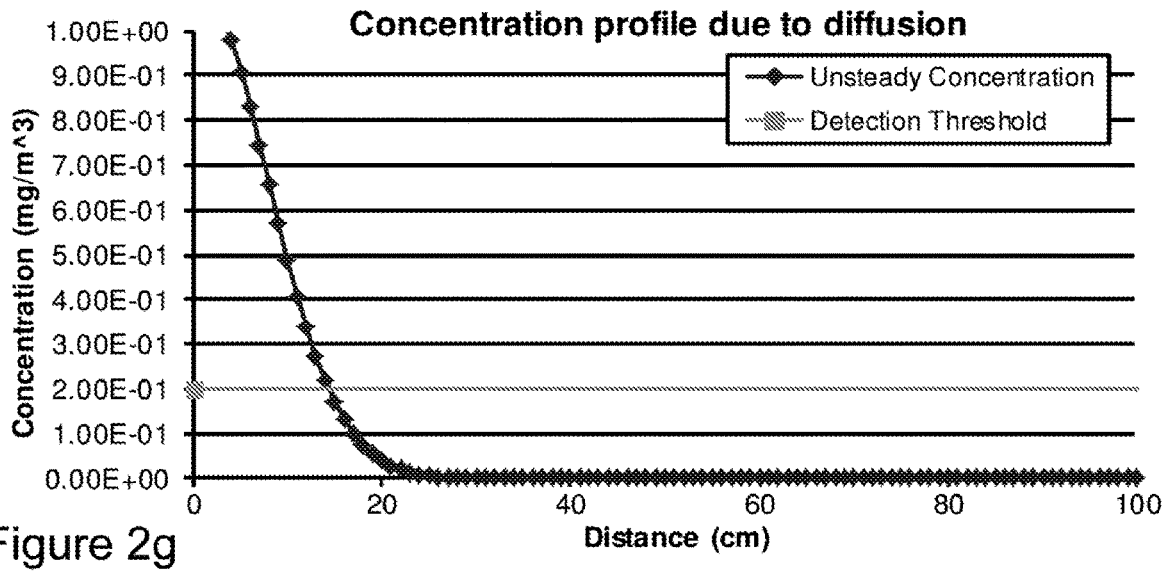
Figure 2H:
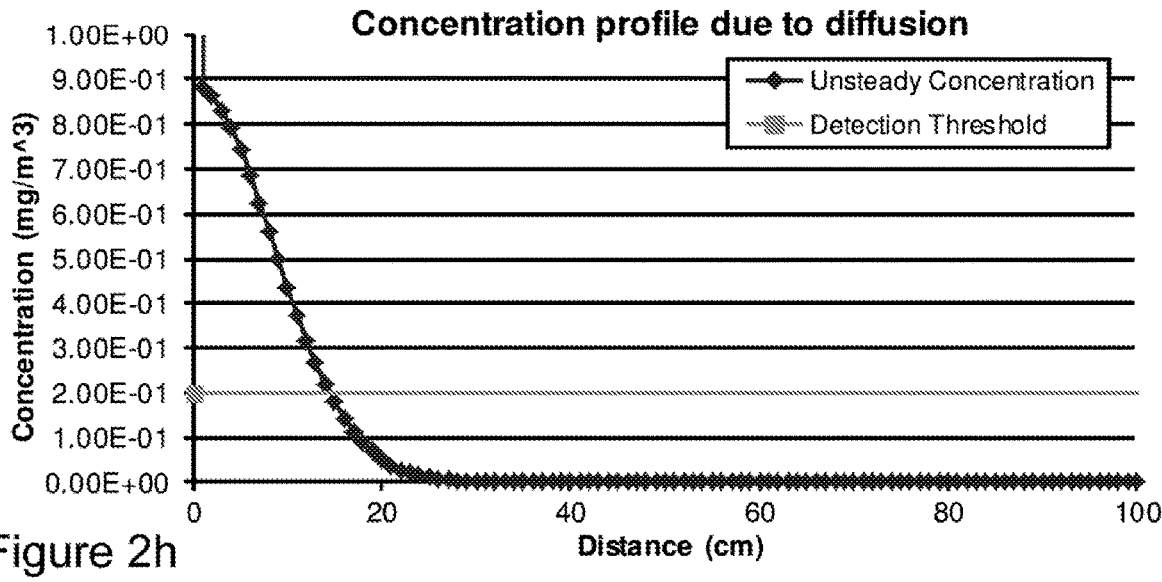
Figure 2I:
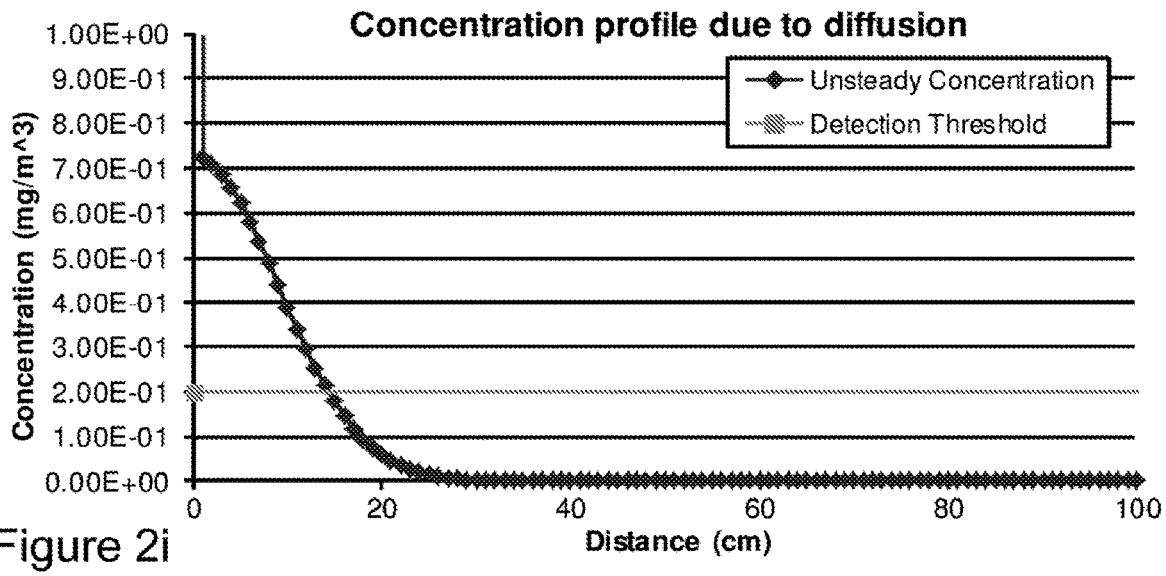
Figure 2J:
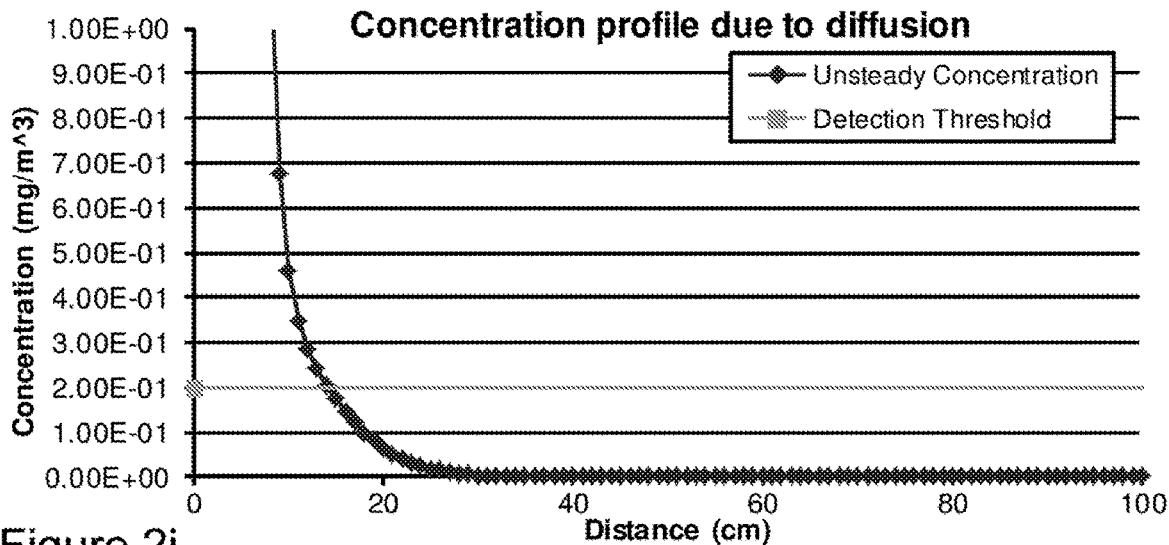
Figure 2K:
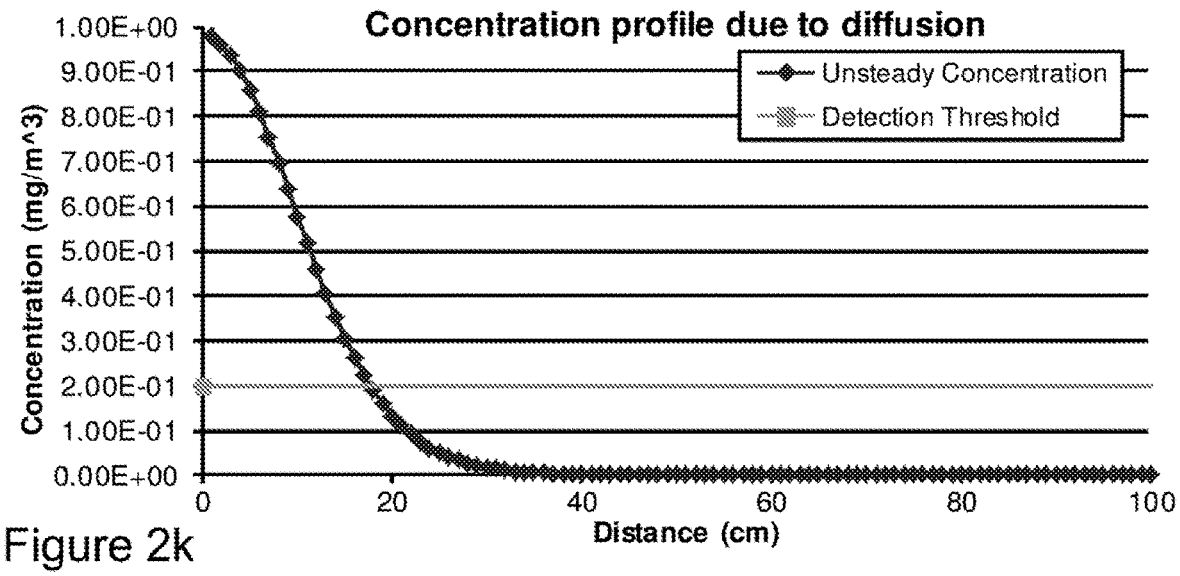
Figure 2L:
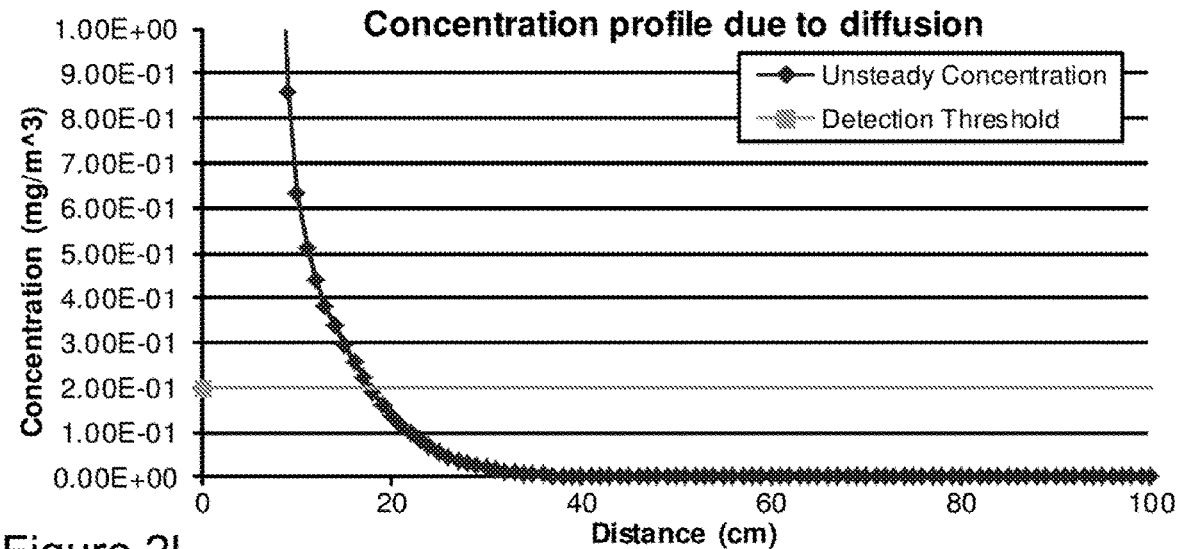

With these values the concentration profile due to diffusion has the time evolution shown in FIGS. 2a-2f. FIG. 2a shows the concentration profile before any scent has been dispensed, FIG. 2b after an initial squirt, and the subsequent time evolution in FIGS. 2c, 2d, 2e, 2f, 2g, 2h, and then a further increase in concentration in FIG. 2j following the next squirt. FIGS. 2k and 2l show the concentration immediately before and after the subsequent squirt, showing how a stead state scent bubble is approximated.

The corresponding distances where the detection threshold is reached are

| FIG. | Distance to detection threshold (cm) |
|---|---|
| 2b | 17.59 |
| 2c | 23.15 |
| 2d | 27.04 |
| 2e | 30.09 |
| 2f | 32.64 |
| 2g | 34.82 |
| 2h | 36.74 |
| 2i | 38.45 |
| 2j | 40.00 |
| 2k | 47.87 |
| 2l | 48.71 |

These assume that every 45 seconds a new spray is emitted, and it can be seen that after an initial build up the concentration is kept above the detection threshold within 40 cm of the device.

Figure 3:
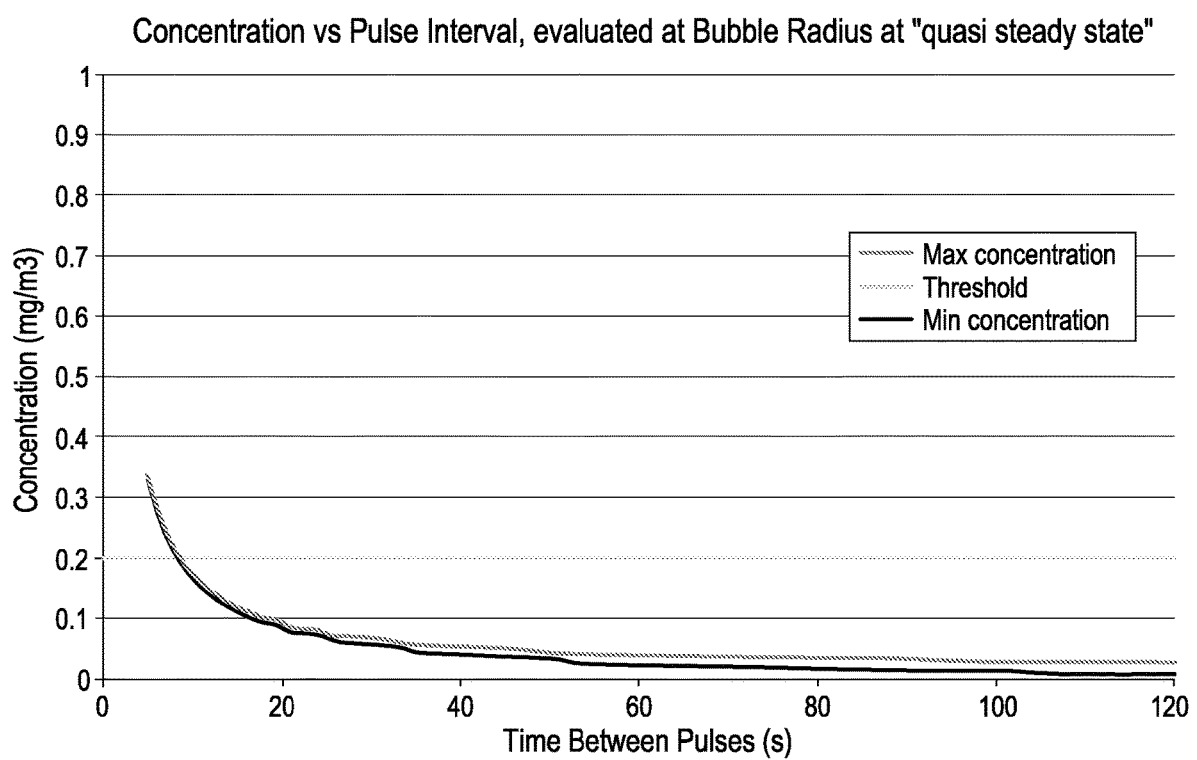
FIG. 3 shows a graph of scent concentration against pulse interval.

Referring now to FIG. 3, this shows a graph of scent concentration against vs pulse interval, evaluated at the bubble radius in a "quasi steady state" condition. The graph is evaluated at a specified bubble radius, and at a time given by a multiple of the characteristic time, which is intended to approximate the steady state solution. The threshold level is set at 0.2 mg/m³.

The graph of FIG. 3 can be used to determine a (longest) spray interval that ensures the minimum concentration does not drop below a define, e.g. detection, threshold. The skilled person will appreciate from the above example and calculations that a graph of the type shown in FIG. 3 may be plotted given the threshold concentration and a target scent bubble radius, and hence may be used to determine, the interval between pulses (pulse interval) for a pulse volume (or equivalently, pulse mass). The pulse interval and pulse volume may be determined for a device. Optionally a set of data may be obtained, in a corresponding manner, for a range of pulse intervals and/or for a range of pulse volumes and/or for a range of different perfumes (i.e. detection thresholds) or perfume combinations. Optionally such data may be obtained for each of one or more high and/or mid and/or low note ingredients so that a pulse volume and/or interval may be selected according to the selected ingredients, for example in a device such as that described later where a perfume or the ingredients of a perfume may be manually selected (e.g. by a user) or automatically selected (e.g. according to sensor or other data).

Where a system dispenses multiple perfumes, or perfume components which mix for example in the air after dispensing, different pulse volumes and/or pulse intervals may be selected for the different perfumes/components. For example one perfume/component may be topped up at a different rate (pulse interval) to another. For example where the system dispenses two or more of top, middle and bass note components separately a more rapidly dispersing (diffusing) component may be topped up with a shorter pulse interval than another component or components. In implementations the aim is to maintain an approximate balance of the different components over time.

Graphs such as that shown in FIG. 3 may also be used to examine the sensitivity of the system, for example the difference between maximum and minimum concentrations at the given bubble radius. Long times between pulses will tend to give large swings between max and min concentrations experienced by the user, which may not be desirable.

Wearable Devices/Systems

Figure 4:
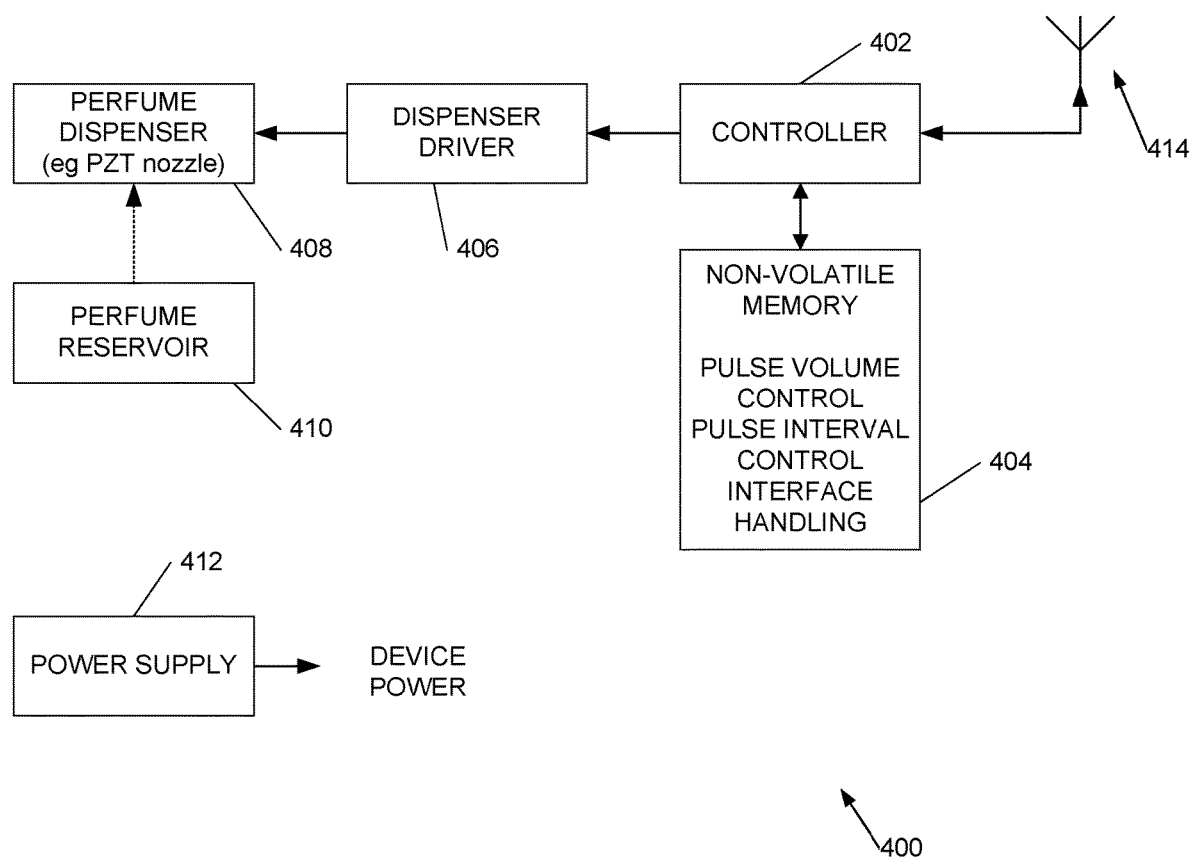
FIG. 4 shows a block diagram of an example wearable scent dispensing device configured to create and maintain a scent bubble.

FIG. 4 shows a block diagram of an example wearable scent dispensing device 400 configured to create and maintain a scent bubble using the method described above. The device comprises controller such as a microcontroller 402 coupled to non-volatile program memory 404 storing code for controlling the device. The controller is also coupled to a dispenser driver 406, coupled to a dispenser 408, such as a PZT nozzle, which receives perfume for dispensing perfume or other liquid from a reservoir 410. The device has a power supply 412, which may be rechargeable, optionally wirelessly. Optionally the device has a wireless interface 414, which may be employed to set up and control the device, for example to define the size of the scent bubble, control the device on/off, provide an external trigger and the like; an interface may be provided by a mobile phone for example via a Bluetooth link.

The code in memory 404 controls the device to provide scent pulses at the determined pulse interval and may also controls the device to provide scent pulses at the determined pulse volume, by controlling the drive to the driver; alternatively the pulse volume may be determined by design. Memory 404 also stores optional device interface code for a wired and/or wireless interface as described above.

In an example device parameters were as below (these values accord with the previously given examples):

Perfume Characteristics:

| | | |
|---|---|---|
| Diffusion Coefficient (which defines the speed with which the molecules dissipate) | 5.00E−04 | m^2/second |
| Density (liquid) | 1 | g/cm^3 |
| Density (vapour)/Density (air) | 5 | |
| Threshold Concentration (level for the scent to be detectable) | 0.2 | mg/m^3 |

Nozzle Parameters:
25 um drops, 1000 drops per pulse

The scent (perfume) dispenser typically dispenses a spray of small droplets. The preceding calculation uses the mass of perfume dispersed per pulse and is not affected by the individual droplet size. However, small droplets will evaporate faster and thus more, smaller drops is better than few, larger drops. With smaller droplets there is also less chance of the droplets reaching and damaging clothing. An example cartridge may have a capacity of around 1 ml.

It is also possible to define a characteristic time for the device, that is a measure of how quickly the system will approach steady-state. This is something like a half-life and is dependent upon bubble radius and diffusion coefficient. In the present example system the characteristic time was 11.25 sec. Scent level calculations may be made at multiples of the characteristic time, and the wearable performance may be evaluated after a quasi-steady state has been reached. However an evaluation time more than a minute or two is questionable, as diffusion and movement effects will then dominate the diffusion processes, and steady state may not be reached. In an example embodiment the time between pulses was 8 seconds. In the present example the cartridge life was then 16.98 days, assuming 16 hr/day usage.

Figure 5:
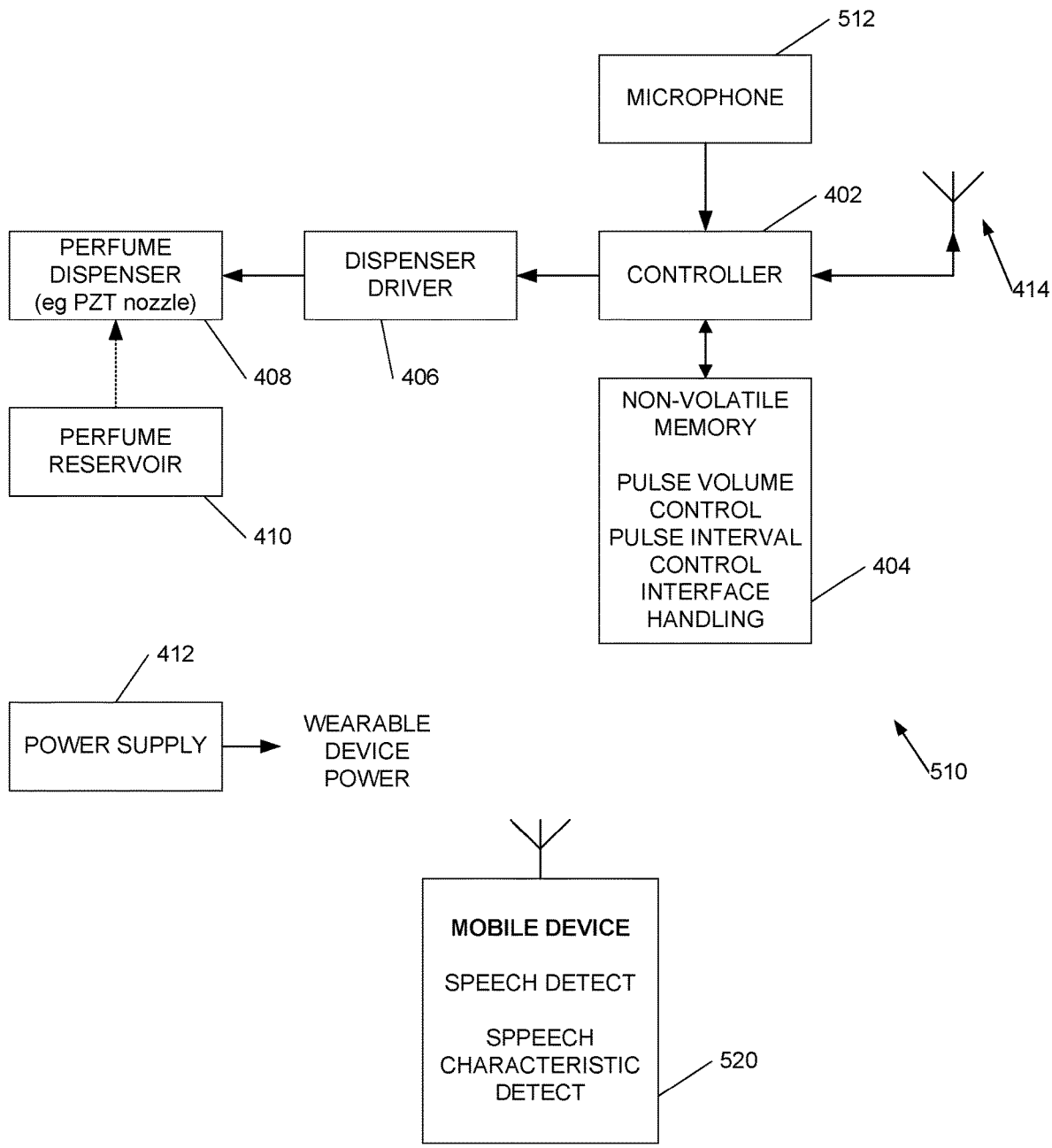
FIG. 5 shows a block diagram of an example of a voice-sensitive wearable scent dispensing system.

FIG. 5 shows a block diagram of an example of a voice-sensitive wearable scent dispensing system 500; similar elements to those of FIG. 4 are indicated by like reference numerals. The system includes a voice-sensitive wearable scent dispensing device 510 coupled to a mobile device 520 such as a mobile phone, for example via a wireless link such as a Bluetooth™ link.

In some implementations the device 510 includes a microphone 512 and the interface handling code may be configured to control the controller 402 to capture sound from the microphone 512 and to communicate the captured and digitised sound to mobile device 520. To conserve batter power short sections of sound may be captured at intervals, for example 10 seconds every 5 minutes. The mobile device may store speech detect code to detect the presence of speech, and may then control device 510 to capture the speech sound substantially continuously and pass corresponding captured speech data to the mobile device 520.

In some other implementations the device 510 omits microphone 512 and instead a microphone of the mobile device 520 is employed to capture speech data.

The mobile device may include speech characteristic detect code to detect a characteristic of the speech such as stress or a manic state of the speaker (distinguishable, for example, by speech pitch/tone and/or increased speech rate). The speech characteristic detect code may comprise, for example, code to implement a trained neural network to classify the captured speech data into one of a plurality of categories; prior to classification the speech data may be converted from the time to the frequency domain. The categories may include one or more of: normal speech, stressed speech, manic speech. Suitable techniques for such classification. Various techniques for analysing speech in this way are known.

The system 500 may be configured to create and maintain a scent bubble in response to detection of the speech characteristic, for example as previously described. Alternatively the system may simply dispense perfume in response to detection of the speech characteristic, without necessarily attempting to maintain a scent bubble. The system may dispense a calming aroma such as lavender; additionally or alternatively the system may dispense a calming or other drug, for example to reduce the stress or mitigate the mania and/or depression.

Other stress reducing aromas which may be dispensed include, but are not limited to: citrus oil (e.g. neroli), bergamot, sweet orange, and sandalwood.

Figure 6:
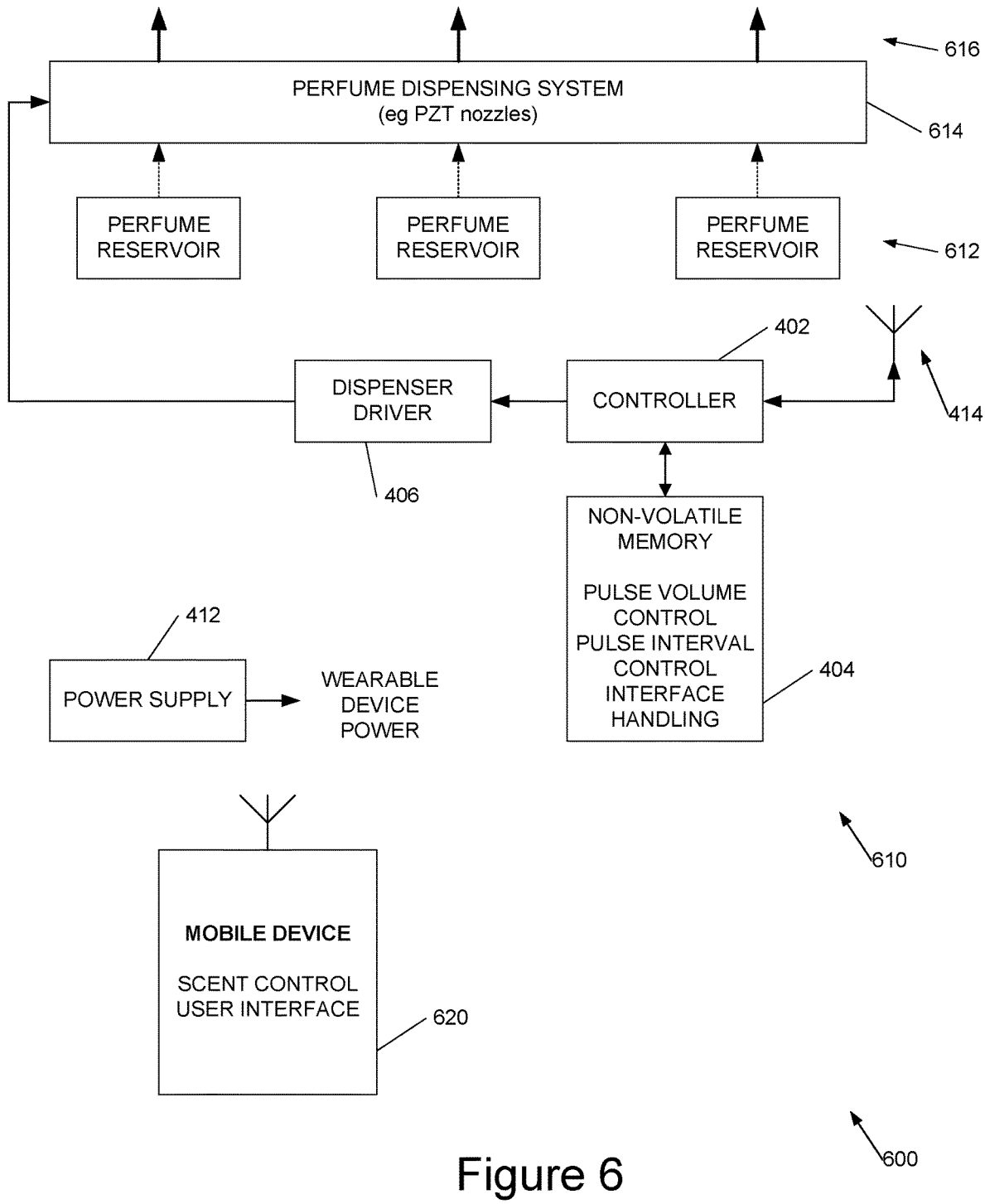
FIG. 6 shows a block diagram of an example of a user-controllable wearable scent dispensing system.

FIG. 6 shows a block diagram of an example of a user-controllable wearable scent dispensing system 600. The system includes a user-controllable wearable scent dispensing device 610 coupled to a mobile device 620 such as a mobile phone, for example via a wireless link such as a Bluetooth™ link.

The dispensing device 610 has a plurality of perfume reservoirs 612 each coupled to dispense perfume from a respective nozzle 616 via a perfume dispensing system 614. A separate perfume dispenser may be provided for each reservoir or a common dispensing system may be used for the reservoirs. In general the perfume dispensing system 614 may comprise one or more piezoelectric transducer (PZT) controlled nozzles. Each nozzle may, for example, squeeze a tube to dispense a spray of droplets from a respective nozzle; dispensers of this type are generally known.

In some implementations each reservoir holds a different perfume; in other implementations each reservoir may holds a different perfume ingredient, for example a top, middle and bottom note ingredient. Whether or not a user interface is present, a system in which each reservoir holds a different perfume ingredient may be controlled as previously described to top up different components of the scent by employing different pulse volumes and/or pulse intervals, for example to compensate for dispersal (diffusion) of the ingredients through the air at different rates.

As illustrated in FIG. 6, mobile device 620 may implement a scent control user interface to enable a user to select perfume from one of the reservoirs and/or to control a proportion of the perfume ingredients to change the dispensed scent. Optionally multiple different ingredients for each of multiple scent notes (e.g. top and/or middle and/or bottom notes) may be provided to enable a greater range of scents to be dispensed. The user may then be enabled to control which ingredients are employed additionally or alternatively to their proportions.

The system of FIG. 6 may be used in conjunction with the previously described techniques to create and maintain a bubble of the desired scent. Alternatively the system may be employed independently of the scent bubble technique— that is the system may be employed to facilitate user control of a dispensed scent without control of the pulse volume and/or interval to maintain a scent bubble.

The scent control user interface may allow the user to directly control the scent ingredients and/or their proportions, or the interface may allow the user to define a target scent in terms of one or more experiential dimensions, for example in terms of fragrance notes and/or fragrance families and/or using a fragrance wheel, and/or using descriptors.

Figure 7:
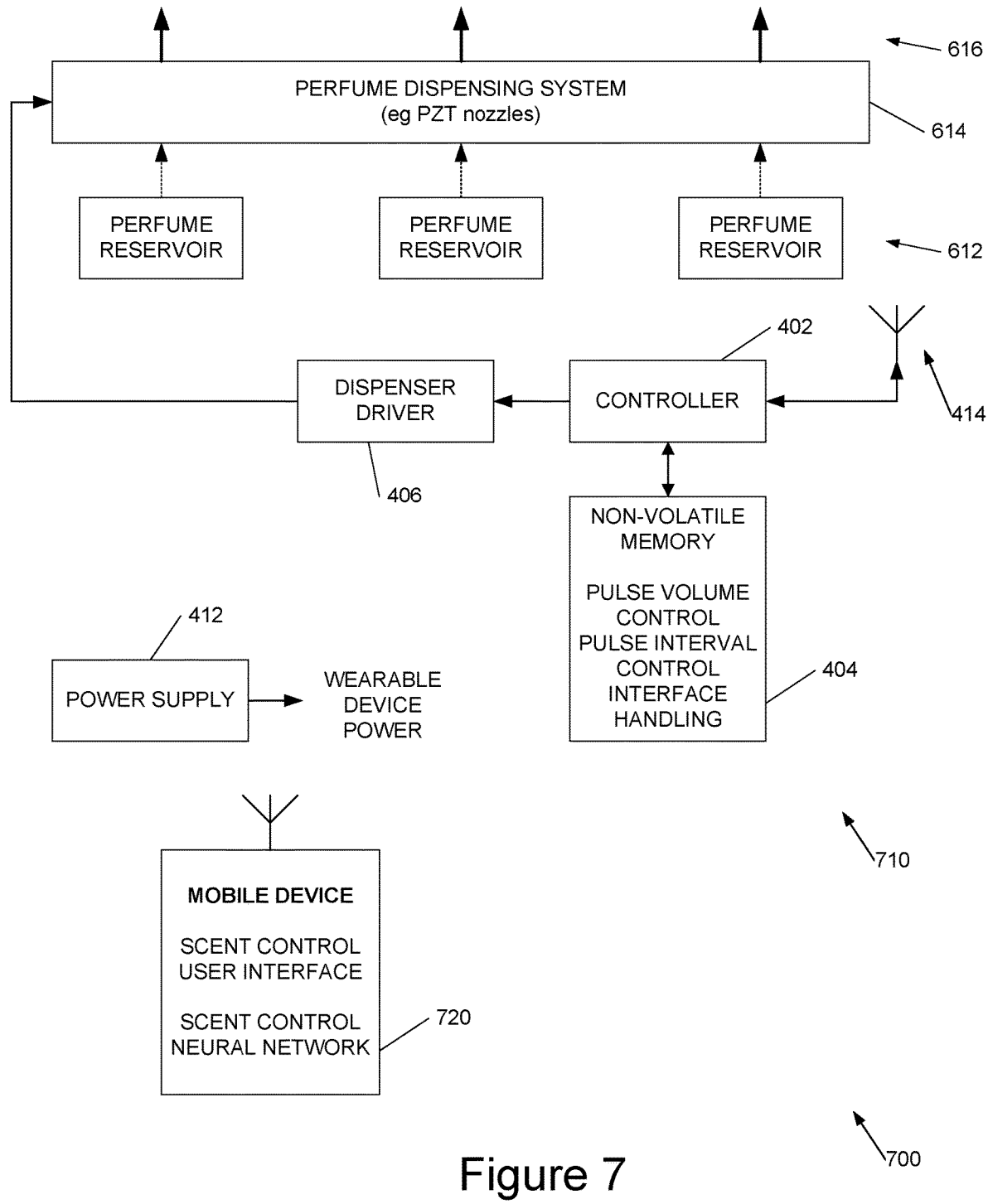
FIG. 7 shows a block diagram of an example of a machine-learning based wearable scent dispensing system.

FIG. 7 shows a block diagram of an example of a machine-learning based wearable scent dispensing system 700. The system includes a wearable scent dispensing device 710 coupled to a mobile device 720 such as a mobile phone, for example via a wireless link such as a Bluetooth™ link.

The mobile device 720 optionally includes a scent control user interface as previously described, for training purposes; alternatively the system may employ training data from other users or may implement a previously trained control system or neural network.

The mobile device 720 is configured to collect user scent control data from the scent control user interface and also associated context data. The context data may comprise, for example, one or more of: time of day, day of week, location, activity data (e.g. is the user sitting, walking, running, dancing and so forth), voice data (e.g. processed as previously described), music data (e.g. relating to a played music genre); and may also include user identification data.

For example in some implementations the system, for example mobile device 720, may detect the sentiment of a song and select, and optionally dispense, a scent dependent upon the detected sentiment. The scent to select/dispense may, but need not have been, learned by a machine learning system such as a neural network. The sentiment of a song may be determined by classifying the song, for example using a neural network, into one of a plurality of sentiment categories. The scent may be selected dependent upon the sentiment category into which the song is classified with the aim of matching the taste or mood of the user e.g. revitalising/energising scent to accompany uplifting music or a relaxing scent for mellow music. In a related manner the system, for example mobile device 720, may detect a music or other recommendation and select, and optionally dispense, a scent dependent upon the music or other recommendation. As described elsewhere in this specification, selecting a scent may involve selecting from one or more perfumes (fragrances) or perfume (fragrance) ingredients.

Additionally or alternatively in implementations the system, for example mobile device 720, may detect a contemporaneous scheduled or other event, for example from an electronic calendar, social media or the like and select, and optionally dispense, a scent dependent upon the scheduled or other event.

The mobile device 720 may also include a dispensing/scent control neural network; this may be pre-trained or may learn the one or more user's preferences. In implementations the dispensing/scent control neural network receives the context data as input data and outputs dispensing/scent control data which is sent to the wearable device over the communications link to control the dispensed liquid/scent. As previously, a scent bubble may or may not be created and maintained. The dispensing/scent control data may comprise one or more of pulse interval data and pulse volume data for one or more perfume reservoirs, and/or reservoir selection data (e.g. to select a perfume and/or perfume component). The scent may be controlled simply by controlling the intensity or scent bubble size in a device with a single reservoir; or more complex control may be employed.

In a device which learns the user's preferences the dispensing/scent control neural network may be trained using a supervised learning technique by providing the context data as input to the neural network and training the neural network to reproduce the user scent control data, for example by back propagating a gradient dependent upon a difference between the neural network output and user scent control training data. The neural network may be a feedforward neural network, for example it may comprise a convolutional neural network.

No doubt many other effective alternatives will occur to the skilled person. It will be understood that the aspects of the disclosed embodiments are not limited to the described embodiments and encompasses modifications apparent to those skilled in the art lying within the spirit and scope of the claims appended hereto.

The invention claimed is:

1. A method of creating and maintaining a personalized bubble of scent, the method comprising:

providing a wearable device comprising a perfume reservoir, a perfume dispenser coupled to a scent reservoir, and a controller;

controlling said wearable device to dispense a pulse volume of perfume from said scent reservoir at a pulse interval; and determining said pulse volume and said pulse interval to maintain a mass per unit volume concentration of said perfume above a threshold level within a defined radius from said wearable device.

2. The method as claimed in claim 1 wherein said threshold level is an average human nasal detection threshold for the scent.

3. The method as claimed in claim 1 wherein said mass per unit volume concentration of said perfume is determined from a minimum over time, t, or from an integral over $$C(r, t) = f\left(M, \frac{r^2}{4Dt}\right)$$

time, t, of C(r,t) where where r is the radius, M is a mass of scent material per pulse volume, D represents a diffusivity of the scent, and f( ) is a function representing diffusion of the scent in 3D space.

4. The method as claimed in claim 1 further comprising using said perfume undiluted in said perfume reservoir.

5. The method as claimed in claim 1, wherein said radius is less than 100 cm and wherein said pulse volume is less than 1 nanolitre.

6. The method as claimed in claim 1 further comprising providing a user interface to enable a user to control the scent; and in response to user scent control data from the user interface selecting one or more perfume reservoirs from a plurality of perfume reservoirs.

7. The method as claimed in claim 1 further comprising holding different perfume ingredients, and using different pulse volumes and/or pulse intervals to control dispensing from different perfume reservoirs in order to compensate for different respective dispersal rates of the perfume ingredients in the reservoirs.

8. The method, as claimed in claim 1, comprising inputting context data relating to a use context of the wearable device; providing the context data to a scent control neural network, wherein the scent dispensed by a wearable device is dependent upon a scent control data.

9. The method as claimed in claim 8 further comprising providing a user interface to enable a user to control the scent, and training the scent control neural network or another neural network using a user scent control data from the user interface and corresponding context data.

10. The method as claimed in claim 8 wherein the context data comprises music data identifying or classifying music currently heard by a wearer of the wearable device.

11. A non-transitory data carrier carrying processor control code to implement the method of claim 1.

12. A wearable device comprising:
a liquid reservoir;
a liquid dispenser coupled to the liquid reservoir; and
a controller to dispense a pulse volume of liquid from the wearable device at a pulse intervals,
such that said pulse volume and said pulse interval maintain a mass per unit volume concentration of said liquid above a threshold level within a defined radius from said wearable device.

13. The wearable device as claimed in claim 12 wherein the wearable device has an acoustic transducer, and wherein the acoustic transducer is coupled to a processor to process a speech signal of a wearer of the wearable device to detect one or more speech characteristics of the wearer.

14. The wearable device as claimed in claim 13 wherein the one or more speech characteristics comprise one or more speech characteristics of mania or depression, and wherein a processor is configured to process the speech signal to classify the wearer as in a manic or depressive state.

15. The wearable device as claimed in claim 12, wherein the liquid is a perfume.

16. The wearable device as claimed in claim 15 comprising a plurality of liquid reservoirs, wherein the device has a user interface to enable a user to control a scent; and wherein the device is configured to, in response to user scent control data from the user interface, select one or more liquid reservoirs from the plurality of liquid reservoirs and/or control a pulse volume and/or pulse interval for the said one or more liquid reservoirs.

17. The wearable device as claimed in claim 15 comprising a plurality of liquid reservoirs for holding different perfume ingredients, and wherein the device is configured to use different pulse volumes and/or pulse intervals to control dispensing from the liquid reservoirs.

18. The wearable device as claimed in claim 12 wherein the wearable device includes, or is coupled to, a dispensing control neural network configured to receive use context data, wherein the dispensing control neural network is further configured to output dispensing control data in response to said use context data.

19. A wearable device comprising:
a plurality of perfume reservoirs each for a respective perfume or perfume ingredient;
at least one dispenser coupled to the perfume reservoirs; and
a controller to dispense perfume or a perfume ingredient from the wearable device at intervals;
wherein the controller is configured to control the wearable device to dispense a pulse volume of the perfume or perfume ingredient from each perfume reservoir at a respective pulse interval.

20. The wearable device as claimed in claim 19 wherein the device has a user interface to enable a user to control a respective perfume or perfume ingredient; and wherein the device is configured to, in response to user perfume control data from the user interface, select one or more reservoirs from the plurality of reservoirs and/or control a pulse volume and/or pulse interval for said one or more reservoirs.

21. The wearable device as claimed in claim 19 wherein the device is configured to use different pulse volumes and/or pulse intervals to control dispensing from the reservoirs.

22. The wearable device as claimed in claim 19 wherein the wearable device includes, or is coupled to, a scent control neural network; wherein the scent control neural network is configured to receive use context data and in response to output scent control data for controlling a scent dispensed by a wearable device.

23. A method of calming a person, the method comprising:
providing the person with a wearable device comprising a liquid reservoir, a liquid dispenser coupled to the liquid reservoir, and a controller to dispense a volume of liquid from the wearable device at intervals;
capturing speech data from the person as the person is speaking;
processing the captured speech data to detect one or more characteristics of the speech and, in response, to the detected characteristics:

controlling said wearable device to dispense a pulse volume of liquid from said liquid reservoir at pulse intervals; and controlling said pulse volume and said pulse interval to maintain a lass mass per unit volume concentration of said liquid above a threshold level within a defined radius from said wearable device.

24. The method as claimed in claim 23 comprising processing the captured speech data to detect a state of mania or depression in the person from a voice of the person.

25. The method as claimed in claim 23 wherein said mass per unit concentration of said liquid at greater than said threshold level at a radius r from said wearable device, where said concentration is determined from a minimum over time, t, or from an integral over time, t, of C(r,t) where $$C(r,t) = f\left(M, \frac{r^2}{4Dt}\right)$$

where M is a mass of liquid per pulse volume, D represents a diffusivity of the liquid, and f( ) is a function representing diffusion of the liquid in 3D space.

26. A non-transitory data carrier carrying processor control code to implement the method of claim 23.

* * * * *